United States Patent [19]

Photis

[11] 4,199,420
[45] Apr. 22, 1980

[54] ALKOXYMETHYLBENZOPHENONES AS PHOTOINITIATORS FOR PHOTOPOLYMERIZABLE COMPOSITIONS AND PROCESS BASED THEREON

[75] Inventor: James M. Photis, Ridgefield, Conn.

[73] Assignee: Stauffer Chemical Company, Westport, Conn.

[21] Appl. No.: 10,762

[22] Filed: Feb. 9, 1979

Related U.S. Application Data

[62] Division of Ser. No. 894,052, Apr. 6, 1978.

[51] Int. Cl.$^2$ ............................ C08F 8/00; C08F 2/46
[52] U.S. Cl. ........................ 204/159.15; 204/159.14; 204/159.16; 204/159.19; 204/159.23; 204/159.18; 260/591; 427/54.1; 430/281; 430/923
[58] Field of Search ................... 260/591; 204/159.18, 204/159.23, 159.24, 159.15, 159.16, 159.14; 96/115 P

[56] References Cited

U.S. PATENT DOCUMENTS

| | | | |
|---|---|---|---|
| 3,086,988 | 4/1963 | Gordon | 260/488 |
| 3,536,661 | 10/1970 | Hagemeyer et al. | 260/45.85 |
| 3,849,497 | 11/1974 | Heine et al. | 260/591 |
| 3,998,855 | 12/1976 | Karrer | 260/348 R |
| 4,022,674 | 5/1977 | Rosen | 204/159.22 |
| 4,054,682 | 10/1977 | Kuesters et al. | 427/54 |
| 4,080,275 | 3/1978 | Photis et al. | 204/159.23 |

*Primary Examiner*—Richard B. Turer
*Attorney, Agent, or Firm*—Michael E. Zall

[57] ABSTRACT

Alkoxymethylbenzophenones having the formula:

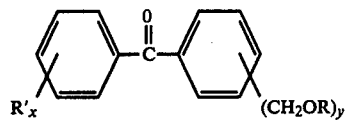

wherein R is hydrocarbon of 1 to 20 carbon atoms, alkoxy-substituted alkylene where the alkylene moiety has 2 to 12 carbon atoms and the alkoxy 1 to 12 carbon atoms or —(CH$_2$CH$_2$O)$_n$—R″ wherein R″ is alkyl of 1 to 12 carbon atoms and n is an integer from 2 to 5; R′ is hydrogen, halogen or —CH$_2$OR; and x and y are independently selected integers from 1 to 5. The alkoxymethylbenzophenones are useful photoinitiators for compositions comprising photopolymerizable ethylenically unsaturated compounds.

15 Claims, No Drawings

ALKOXYMETHYLBENZOPHENONES AS PHOTOINITIATORS FOR PHOTOPOLYMERIZABLE COMPOSITIONS AND PROCESS BASED THEREON

This is a division of application Ser. No. 894,052 filed Apr. 6, 1978.

BACKGROUND OF THE INVENTION

This invention relates to substituted benzophenones, photopolymerizable compositions based thereon and to a method employing same. More particularly, this invention relates to certain alkoxymethylbenzophenones and to their use as photoinitiators for ethylenically unsaturated compounds.

Photopolymerization of unsaturated compositions wherein a photoinitiating compound is included in the polymerizable mass is well known in the art. The process has many advantages over thermal polymerization and is particularly useful where long holding life combined with rapid hardening at low temperature is desirable. Photoinitiating compounds must absorb light and utilize the energy so acquired to initiate polymerization.

A large number of compounds have been found useful as photoinitiators for the polymerization of unsaturated compounds. Among those heretofore in most common usage in industry are the benzoin ethers of primary and secondary alcohols such as methyl alcohol, ethyl alcohol, isopropyl alcohol and isobutyl alcohol.

While particular industrial applications often dictate certain requisite characteristics, the primary determinants of universal application in the selection of a suitable photoinitiating compound are its level of reactivity and its effect upon storage stability when combined with the photopolymerizable medium wherein it is to function. This latter characteristic is significant in view of the desirability of one-component systems which will not gel prior to use.

While compounds in common use as photoinitiators do effect rates of polymerization which are industrially acceptable and render photopolymerization superior to thermal polymerization in various applications, methods of achieving increased polymerization rates with increased stability are constantly being sought. Improved photoinitiators are particularly desirable since photopolymerization techniques are gaining increasingly widespread acceptance due to the inherently lower equipment costs, reduction of volatile emissions and reduced energy consumption which attend their use.

Thus, the ethers of benzoin, which are widely used as photoinitiating compounds, are not wholly satisfactory with regard to the one-component system storage stability factor. Any unsaturated system to which a benzoin ether is added has considerably diminished dark storage stability and will gel prematurely. Various attempts have been made to remedy this deficiency of the benzoin compounds by including stabilizing additives in the polymerization system. Thus, U.S. Pat. No. 3,819,495 discloses the addition of organic chlorine containing compounds and copper compounds as a stabilization system while U.S. Pat. No. 3,819,496 teaches the use of organic chlorine compounds with iron and/or manganese compounds for that purpose. Many other stabilizers have been suggested and, while some improvements have been achieved in the stability of unsaturated systems containing benzoin-type photoinitiators, the necessity of incorporating stabilizing additives raises the cost of such systems appreciably while the results are still not wholly satisfactory.

Thus, various aromatic compounds have been proposed as photoinitiators for unsaturated compounds. For example, U.S. Pat. No. 3,715,293 teaches the use of acetophenone compounds such as 2,2-diethoxyacetophenone, while a series of patents including U.S. Pat. Nos. 3,926,638; 3,926,639; 3,926,640; 3,926,641; 4,022,674; 4,004,998; 4,008,138 and 4,028,204 describe complex compounds derived from benzophenone. As an example of the benzophenone-derived materials, U.S. Pat. No. 3,404,998 describes photoinitiators made by reacting carboxy-substituted benzophenones with hydroxylcontaining polyethylenically unsaturated esters, while U.S. Pat. Nos. 3,926,639 and 4,028,204 describe a benzophenone substituted with a carboxy group and an ester group which is reacted with certain resins, such as alkyds, polyesters, polyethers, polyamides and epoxides, to provide the photoinitiator. In U.S. Pat. No. 3,998,712, monoketals of diketones are disclosed as photoinitiators.

Another approach is disclosed in U.S. Pat. No. 3,759,807 where certain benzophenones which must be used with activators are disclosed. Also representative of benzophenone systems is Brit. Pat. No. 1,223,463 which teaches the addition of diketones such as m-benzoylbenzophenone, ethylene glycol bis (p-benzoylbenzoate) or diethylene glycol bis (p-benzolybenzoate) to nylon to give photosensitive materials suitable for the preparation of printing plates.

In U.S. Pat. No. 4,017,652, ethyl benzoylbenzoate is disclosed as a photosensitizer which must be used in connection with a photoinitiator such as a benzoin ether, while copending application Ser. No. 817,089 describes the use of p-benzoyl benzoates or p-benzoyl benzamides as photoinitiators.

Now it has been found in accordance with this invention that certain alkoxymethylbenzophenones are excellent photoinitiators for ethylenically unsaturated compounds. These photoinitiators provide polymerizable systems not subject to premature gelation. Furthermore, these photoinitiators are reactive in many different systems based on ethylenically unsaturated compounds.

SUMMARY OF THE INVENTION

The substituted benzophenones of this invention are mono and polyalkoxymethylbenzophenones. The photopolymerizable composition of this invention comprises an ethylenically unsaturated compound and the alkoxymethylbenzophenone. After applying the compositions to the desired substrate, curing is effected by exposure to actinic radiation.

DETAILED DESCRIPTION OF THE INVENTION

More in detail, the alkoxymethylbenzophenones of this invention have the formula:

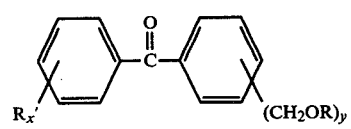

wherein R is hydrocarbon of 1 to 20 carbon atoms, alkoxysubstituted alkylene where the alkylene moiety has 2 to 12 carbon atoms and the alkoxy of 1 to 12 carbon atoms or —$(CH_2CH_2O)_n$—R" wherein R" is alkyl of 1 to 12 carbon atoms and n is an integer from 2 to 5; R' is hydrogen, halogen or -$CH_2OR$; and x and y are independently selected integers from 1 to 5. The alkoxymethylbenzophenones are useful photoinitiators for compositions comprising photopolymerizable ethylenically unsaturated compounds.

In the foregoing definition, the term "hydrocarbon of from 1 to 20 carbon atoms" refers to straight and branched chain acyclic hydrocarbon groups which may contain unsaturated carbon-to-carbon bonds.

Illustrative compounds I include, but are not limited to, 4-(methoxymethyl)benzophenone; 4-(eicosyloxymethyl) benzophenone; 4-(2-propenyloxymethyl)benzophenone; 4-(2-methoxyethoxymethyl)benzophenone; 4-(2-dodecyloxyethyloxymethyl)benzophenone; 4-(2-ethoxydodecyloxymethyl)benzophenone; 4-(methoxymethyl)-4'-chlorobenzophenone; 4-(ethoxymethyl)-2', 4'-dibromobenzophenone; 4,4'-bis-(methoxymethyl) benzophenone; 4-(methoxymethyl)-2', 3', 4', 5', 6'-pentachlorobenzophenone; 4-(methoxymethyl)-4'-fluorobenzophenone; etc.

The alkoxymethylbenzophenones I are prepared by reacting a substituted (chloromethyl)benzophenone with the appropriate alcohol in the presence of alkali metal hydroxide according to the following equation where R, R' and x are as previously described and M is sodium or potassium:

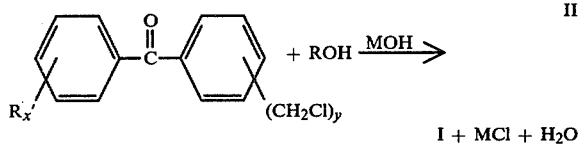

$$I + MCl + H_2O$$

Where poly(alkoxymethyl)benzophenones I are desired, it is preferable to prepare them by chloromethylation of the alkoxymethyl substituted benzophenones II, or by chlorination of the corresponding polymethylbenzophenones.

The reaction is carried out at temperatures above 60° C., and preferably between about 60° C. and 150° C. In order to ensure complete and rapid reaction, it is preferred to employ an excess of the alkali metal hydroxide. The product is readily isolated by conventional techniques, such as filtration, concentration, distillation, etc.

The compositions curable by actinic radiation according to the invention can contain a photopolymerizable polymer in a reactive ethylenically unsaturated monomeric medium, a reactive polymer alone, a reactive monomer alone, or any of these combined with an inert solvent. Additionally, the polymerizable composition can contain any of the pigments commonly used in photopolymerization techniques.

Polymerizable ethylenically unsaturated compounds which are useful in practicing the invention are acrylic, α-alkacrylic and α-chloroacrylic acid compounds such esters, amides and nitriles. Examples of such compounds are acrylonitrile, methacrylonitrile, methyl acrylate, ethyl acrylate, methyl methacrylate, isobutyl methacrylate, 2-ethylhexyl acrylate, methacrylamide and methylα-chloroacrylate. Also useful, although not preferred due to their slower rates of reactivity, are vinyl and vinylidene esters, ethers and ketones. Additionally, compounds having more than one terminal unsaturation can be used. Examples of these include diallyl phthalate; diallyl maleate; diallyl fumarate; triallyl cyanurate; triallyl phosphate; esters of polyols and α,β-unsaturated acids such as ethylene glycol dimethylacrylate, glycerol trimethacrylate, pentaerythritol triacrylate, pentaerythritol tetraacrylate and trimethylolpropane triacrylate; methacrylic anhydride; and allyl ethers of monohydroxy or polyhydroxy compounds such as ethylene glycol diallyl ether, pentaerythritol tetraallyl ether, and the like. Nonterminally unsaturated compounds such as diethyl fumarate can similarly be used.

The acrylic acid derivitives are particularly well suited to the practice of the invention and are consequently preferred components as monomers in monomer-containing polymerizable systems and as reactive centers in polymerizable polymers. While monomeric styrene can be used in the practice of the invention, it is not a preferred constituent of systems polymerizable thereby due to its slow rate of reaction.

Additionally, the photopolymerizable composition can contain a sensitizer capable of enhancing the photoinitiating reactivity of the photoinitiating compound of the invention by triplet sensitization. Examples of sensitizers useful in the practice of the invention are such compounds as biphenyl, xanthone, thioxanthone, acetophenone and the like. These are typically added in amounts ranging from about 0.1 to about 6 weight percent. The techniques whereby such sensitizers are selected for use in conjunction with particular photoinitiators are well known in the art. See, for example MUROV, Handbook of Photochemistry, Marcel Dekker, Inc., New York (1973).

Additionally polymerization promoters such as organic amines can be used to accelerate cure rates, either alone or in combination with a sensitizer. Such amines can be primary, secondary, or preferably, tertiary, and can be represented by the general formula:

$$R^1R^2R^3N$$

wherein $R^1$ and $R^2$ are independently selected hydrogen, straight chain or branched alkyl having from 1 to about 12 carbon atoms, straight chain or branched alkenyl having from 2 to about 12 carbon atoms, cycloalkyl having from 3 to about 10 ring carbon atoms, cycloalkenyl having from 3 to about 10 ring atoms, aryl having from 6 to about 12 ring carbon atoms, alkaryl having 6 to about 12 ring carbon atoms; $R^3$ has the same meaning as $R^1$ and $R^2$ with the exception that it cannot be hydrogen and that it cannot be aryl when both $R^1$ and $R^2$ are aryl. Also when taken together $R^2$ and $R^3$ can be divalent alkylene group having from 2 to about 12 carbon atoms, a divalent alkenylene group having from 3 to about 10 carbon atoms, a divalent alkadienylene group having from 5 to about 10 carbon atoms, a divalent alkatrienylene group having from 5 to about 10 carbon atoms, a divalent alkyleneoxyalkylene group having a total of from 4 to about 12 carbon atoms, or a divalent alkyleneaminoalkylene group having a total of from 4 to about 12 carbon atoms. As previously indicated, the amines can be substituted with other groups; thus, the $R^1$, $R^2$ and $R^3$ variables, whether taken singly or together, can contain one or more substituents thereon. The nature of such substituents is generally not of significant importance and any substituent group can be present that does not exert a pronounced deterrent effect on the ultraviolet crosslinking reaction.

Exemplary suitable organic amines are methylamine, dimethylamine, triethylamine, isopropylamine, triisopropylamine, tributylamine, t-tubylamine, 2-methylbutylamine, N-methyl-N-butylamine, di-2-methylbutylamine, tri-2-ethylhexylamine, dodecylamine, triethanolamine, methyl-diethanolamine, propanolamine, triisopropanolamine, butylethanolamine, dihexanolamine, 2-methoxyethylamine, 2-hydroxyethyldiisopropylamine, allylamine, cyclohexylamine, trimethylcyclohexylamine, bis-methylcyclopentylamine, tricyclohexadienylamine, N-methyl-N-cyclohexylamine, N-2-ethylhexyl-N-cyclohexylamine, diphenylamine, methylphenylamine, trixylylamine, tribenzylamine, triphenethylamine, benzyldimethyl, N-methylethylenimine, N-cylohexylethylenimine, piperidine, N-ethylpiperidine, 1,2,3,4-tetrahydropyridine, 2-, 3- and 4-picoline, morpholine, N-methyl morpholine, N-2-hydroxyethylmorpholine, piperazine, N,N'-dimethylpiperazine, 2,2-dimethyl-1,3-bis[3(N-morpholinylpropionyl]-propane, and the like. The preferred organic amines are the tertiary amines, with the alkanol amines being most preferred.

Thus it is seen that the constitution of photopolymerizable compositions which can be used in the practice of the invention is widely variable. However, the compounds enumerated above are purely illustrative. Materials subject to polymerization by actinic radiation as well as permissable variations and substitutions of equivalent components within particular types of compositions are well known to those skilled in the art.

The alkoxymethylbenzophenones I of the invention can be utilized in amounts ranging from about 0.01 to about 30 percent by weight based on the photopolymerizable composition. However, preferable amounts of the compounds are between 1.0 and 6.0 weight percent.

The process can be carried out by mixing a quantity of a photoinitiating compound of the invention with a photopolymerizable composition and exposing the resultant mixture to actinic radiation. Alternatively, a one-component system comprising the photopolymerizable composition, the photoinitiator of the invention and, if desired, pigmentation, can be stored in the dark for a prolonged period of time prior to use without fear of gelation.

A preferred manner of practicing the invention is by the use of photopolymerizable molding and coating compositions which consist of mixtures of unsaturated polymeric compounds and monomeric compounds co-polymerizable therewith. The polymeric compounds can be conventional polyesters prepared from unsaturated polycarboxylic acids such as maleic acid, fumaric acid, glutaconic acid, itaconic acid, citraconic acid, mesaconic acid and the like, and polyhydric alcohols such as ethylene glycol, diethylene glycol, glycerol, propylene glycol, 1,2-butanediol, 1,4-butanediol, pentaerythritol, trimethylolpropane and the like. The carboxylic acid content can also contain saturated components. The inclusion of a monobasic fatty acid content, either as such or in the form of a triglyceride or oil, in the photopolymerizable polyester composition to comprise an alkyd resin is also acceptable. These resins can, in turn, be modified by silicones, epoxides, isocyanates, etc., by known techniques.

The compositions of the instant invention after being prepared in the ratios as set out above can be applied to the material to be coated by conventional means, including brushing, spraying, dipping and roll coating techniques, and may, if dried under ambient or elevated conditions to provide coatings on the substrate. The substrate can be of any composition, including but not limited to plastic, fiber, ceramic, glass, etc.

After the composition is applied to the desired substrate, it is exposed to light radiation having wave lengths of above about 2000 Angstrom units, preferably from about 2000 up to about 8000 Angstroms, and most preferably between about 2400 Angstroms and 5400 Angstroms. Exposure should be from a source located about 1 to 5 inches from the coating for a time sufficient to cause crosslinking of the composition.

The light radiation can be ultraviolet light generated from low, medium, and high pressure mercury lamps. This equipment is readily available and its use is well known to those skilled in the art. Other sources could include electron beam radiation, plasma arc, laser beams, etc.

While any of the compounds having the formula I can be used in the practice of this invention, preferred are those compounds where R' is hydrogen, R is alkyl of 1 to 12 carbon atoms, and x is 5 and y is 1 and particularly where R is lower alkyl, i.e., alkyl of 1 to 4 carbon atoms.

The following examples will serve to illustrate the practice of this invention.

EXAMPLE 1

To a mechanically stirred solution of 1000 grams (7.12 moles) of benzoylchloride in 6000 grams of toluene was added 1000 grams (7.50 moles) of anhydrous aluminum chloride over a 20-30 minute period. The temperature of the reaction mixture rose to near the boiling point during the addition, and heating at reflux was maintained for three additional hours. After cooling, 1200 milliliters of water were added, slowly at first, followed by 1000 milliliters of concentrated hydrochloric acid. The organic layer was separated, washed twice with hot water and concentrated by simple distillation. Vacuum distillation of the residual oil provided 1300 grams (93% yield) of white, semi-solid methyl benzophenone; (b.p. 180°-200° C., 10-15 mm Hg; m.p. 50°-55° C.). The infrared spectrum revealed a carbonyl band at 1660 cm$^{-1}$.

The amount of 912 grams (4.65 moles) of methyl benzophenone was then melted and heated to 100°-110° C. in a two-liter, two-necked, round bottom flask with magnetic stirring. Chlorine gas was introduced through a gas dispersion tube immersed below the liquid at a rate such that the characteristic greenish color of chlorine was not detectable in the exiting stream of hydrogen chloride. Initially the reaction was exothermic and no additional external heating was required. After about seven hours the theoretical uptake in weight (160 g) had occured. The hot melt was poured into 6 liters of isopropyl alcohol. This mixture was chilled to −5° to 0° C. and the precipitated solid was removed by suction filtration to provide 618 grams (57% yield) of 4-(chloromethyl)benzophenone, mp 109°-111° C. A carbonyl band at 1670 cm$^{-1}$ was noted in the infrared spectrum.

To 4 liters of absolute methyl alcohol was added 300 grams (4.5 moles) of 85% potassium hydroxide pellets with mechanical stirring. The amount of 618 grams (2.7 moles) of 4-(chloromethyl)benzophenone was added to the resulting warm solution. The reaction mixture was refluxed for three hours, filtered with suction, and concentrated. Water was added and the lower oily layer was separated and distilled to provide 530 grams (88.5% yield) of 4-(methoxymethyl)benzophenone as an almost colorless liquid (b.p. 140° C., 0.20 mm Hg). The infrared spectrum revealed a carbonyl band at 1660 cm$^{-1}$. Ultraviolet analysis revealed λ max (ε) at 256 nanometers (18,380).

Proton nuclear magnetic resonance analysis revealed the following where m is a multiplet, s is a singlet, and TMS is tetramethylsilane.

| $\delta^1$ | |
| --- | --- |
| 7.5 | (m, ArH) |
| 4.5 | (s, CH$_2$) |
| 3.3 | (s, CH$_3$) |

[1]In CCl$_4$ relative to TMS

Cure rates were determined in air using as a source of actinic light a PPG Model QC 1202 AN UV Processor manufactured by PPG Industries, Inc. The radiation source for this apparatus consists of two high intensity medium pressure quartz mercury lamps 12 inches in length and each operating at a linear power density of about 200 watts per inch or 2400 watts per lamp. The lamps are housed in an elliptical reflector above a variable speed conveyor belt and each lamp provides a 2-inch band of high flux actinic radiation on the conveyor. This 2-inch exposure area is bordered on both sides by an additional area of 6 inches of medium flux energy for a total radiation area of 6 inches for each lamp. In the curing data presented below, cure rate of the polymerizable composition is presented in feet-per-minute-per-lamp (ft./min./lamp.). Thus, a conveyor belt speed of one foot/min. will, with a 12-inch exposure area for the two lamps, provide 60 seconds of exposure or a cure rate of 0.5 ft./min./lamp. Similarly, a belt speed of 10 ft./min. will provide 6 seconds of exposure or a rate of 5.0 ft./min./lamp while a speed of 20.0 ft./min. will give 3 seconds exposure or a rate of 10 ft./min./lamp, etc.

The cure rates for a 4% by weight loading in two standard test solutions are presented below.

| TEST SOLUTION | CURE RATE (Ft./Min./Lamp) |
| --- | --- |
| TMPTA/EHA ACTOMER X . 80®[1] | 15 |
| EPOCRYL RESIN DRH-303/HDDA[2] | 15 |

[1]42% by weight of trimethylolpropane triacrylate, 17% by weight of ethylhexyl acrylate and 41% by weight of ACTOMER X . 80® Resin, an unsaturated long chain linseed oil alkyd resin, available from Union Carbide Corporation.
[2]50% by weight of EPOCRYL® Resin DRH-303, a diacrylate ester of Bisphenol A epoxy resin available from Shell Chemical Company, 50% by weight 1,6-hexanediol diacrylate available from Celenese Corporation.

EXAMPLE 2

Following the procedure of Example 1, a quantity of 4-(chloromethyl)benzophenone was made.

To 1 liter of absolute ethyl alcohol was added 80 grams (1.2 moles) of 85% potassium hydroxide pellets with mechanical stirring. The amount of 115 grams (0.5 moles) of 4-(chloromethyl)benzophenone was added to the resulting warm solution. The reaction mixture was refluxed for three hours, filtered with suction, and concentrated. Water was added and the lower oily layer was separated and distilled to provide 102 grams (84% yield) of 4-(ethoxymethyl)benzophenone. Infrared analysis revealed the presence of a carbonyl band at 1660 cm$^{-1}$. Ultraviolet analysis revealed λ max (ε) of 256 nanometers (18,360). Proton nuclear magnetic resonance analysis revealed the following where m is a multiplet, s is a singlet, q is a quartet, t is a triplet and TMS is tetramethylsilane.

| $\delta^1$ | |
| --- | --- |
| 7.5 | (m, ArH) |
| 4.5 | (s, CH$_2$) |
| 3.5 | (q, CH$_2$) |
| 1.2 | (t, CH$_3$) |

[1]In CCl$_4$ relative to TMS

Cure rates at 4 weight percent loading in four standard test solutions were determined following the procedure described in Example 1; the results are set forth below.

| TEST SOLUTION | CURE RATE (Ft./Min./Lamp) |
| --- | --- |
| TMPTA/EHA ACTOMER X . 80®[1] | 20 |
| EPOCRYL RESIN DRH-303/HDDA[2] | 15 |
| SUNCURE MONOMER[3] | 10 |
| UVIMER RESIN 540/TMPTA[4] | 7.5 |

[1]42% by weight of trimethylolpropane triacrylate, 17% by weight of ethylhexyl acrylate and 41% by weight of ACTOMER X-80® Resin, an unsaturated long chain linseed oil alkyd resin, available from Union Carbide Corporation.
[2]50% by weight of EPOCRYL® Resin DRH-303, a diacrylate ester of Bisphenol A epoxy resin available from Shell Chemical Company, 50% by weight 1,6-hexanediol diacrylate available from Celenese Corporation.
[3]SUNCURE is a proprietary ethylenically unsaturated resin, available from Sun Chemical Company.
[4]50% by weight Uvimer Resin 540, comprised of 49 parts urethane oligomer B, 19 parts hydroxyethyl acrylate and 32 parts pentaerythritol tetraacrylate, available from Polychrome Corporation, and 50% by weight of trimethylol propane triacrylate.

EXAMPLE 3

4-(Chloromethyl)benzophenone was made following the procedure of Example 1.

To 25 milliliters of 2-methoxyethanol was added, with magnetic stirring, 5.0 grams (0.75 mole) of 85% potassium hydroxide pellets dissolved in 5 milliliters water. The amount of 5.0 grams (0.0216 mole) of 4-(chloromethyl)benzophenone was added, the mixture was refluxed for three hours, filtered with suction, and concentrated. Water was added and the oil which separated was isolated by extraction with ether to provide 5.0 grams (86% yield) of 4-(2-methoxyethoxymethyl)-benzophenone as an orange colored liquid. Infrared analysis revealed the presence of a carbonyl band at 1660 cm$^{-1}$. Ultraviolet analysis revealed λ max (ε) at 256 nanometers (18,380).

Following the procedure of Example 1, cure rates for a 4% by weight loading were determined in two test solutions; the results are reported below.

| TEST SOLUTION | CURE RATE (Ft./Min./Lamp) |
| --- | --- |
| TMPTA/EHA ACTOMER X . 80®[1] | 10 |
| EPOCRYL RESIN DRH-303/HDDA[2] | 7.5 |

[1]42% by weight of trimethylolpropane triacrylate, 17% by weight of ethylhexyl acrylate and 41% by weight of ACTOMER X . 80® Resin, an unsaturated long chain linseed oil alkyd resin, available from Union Carbide Corporation.
[2]50% by weight of EPOCRYL® Resin DRH-303, a diacrylate ester of Bisphenol A epoxy resin available from Shell Chemical Company, 50% by weight 1,6-hexanediol diacrylate available from Celenese Corporation.

What is claimed is:
1. A photopolymerizable composition comprising an ethylenically unsaturated compound and a photoinitiat- ing amount of an alkoxymethylbenzophenone having the formula:

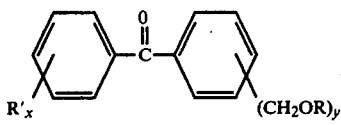

wherein R is hydrocarbon of 1 to 20 carbon atoms, alkoxysubstituted alkylene where the alkylene moiety has 2 to 12 carbon atoms and the alkoxy 1 to 12 carbon atoms or $-(CH_2CH_2O)_n-R''$ wherein $R''$ is alkyl of 1 to 12 carbon atoms and n is an integer from 2 to 5; R' is hydrogen, halogen or $-CH_2OR$; and x and y are independently selected integers from 1 to 5.

2. The composition of claim 1 where said alkoxymethylbenzophenone comprises from about 0.01 to about 30 percent by weight of said composition.

3. The composition of claim 2 wherein R is alkyl of 1 to 12 carbon atoms, R' is hydrogen, x is 5 and y is 1.

4. The composition of claim 3 wherein R is lower alkyl.

5. The composition of claim 4 wherein said alkoxymethylbenzophenone is 4-(methoxymethyl)benzophenone.

6. The composition of claim 4 wherein said alkoxymethylbenzophenone is 4-(ethoxymethyl)benzophenone.

7. The composition of claim 2 wherein R is alkoxysubstituted alkylene where the alkylene moiety has 2 to 12 carbon atoms and the alkoxy 1 to 12 carbon atoms, R' is hydrogen, x is 5 and y is 1.

8. The composition of claim 7 wherein said alkoxymethylbenzophenone is 4[(2-methoxyethoxy)methyl]benzophenone.

9. In the method of photopolymerizing an ethylenically unsaturated compound in the presence of a photoinitiator by exposure to actinic radiation, the improvement which comprises employing as said photoinitiator an alkoxymethylbenzophenone of the formula:

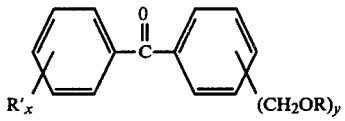

wherein R is hydrocarbon of 1 to 20 carbon atoms, alkoxysubstituted alkylene where the alkylene moiety has 2 to 12 carbon atoms and the alkoxy 1 to 12 carbon atoms or $-(CH_2CH_2O)_n-R''$ wherein $R''$ is alkyl of 1 to 12 carbon atoms and n is an integer from 2 to 5; R' is hydrogen, halogen or $-CH_2OR$; and x and y are independently selected integers from 1 to 5.

10. The method of claim 9 wherein said alkoxymethylbenzophenone comprises from about 0.01 to about 30 percent by weight of said composition.

11. The method of claim 9 wherein in said alkoxymethylbenzophenone R is alkyl of 1 to 12 carbon atoms, R' is hydrogen, x is 5 and y is 1.

12. The method of claim 11 wherein said alkoxymethylbenzophenone is 4-(methoxymethyl)benzophenone.

13. The method of claim 11 wherein said alkoxymethylbenzophenone is 4-(ethoxymethyl)benzophenone.

14. The method of claim 9 wherein in said alkoxymethylbenzophenone R is alkoxysubstituted alkylene where the alkylene moiety has 2 to 12 carbon atoms and the alkoxy 1 to 12 carbon atoms, R' is hydrogen, x is 5 and y is 1.

15. The method of claim 14 wherein said alkoxymethylbenzophenone is 4-[(2-methoxyethoxy)methyl]benzophenone.

* * * * *

UNITED STATES PATENT AND TRADEMARK OFFICE
CERTIFICATE OF CORRECTION

PATENT NO. : 4,199,420
DATED : April 22, 1980
INVENTOR(S) : James M. Photis

It is certified that error appears in the above-identified patent and that said Letters Patent are hereby corrected as shown below:

In the specification, column 2, line 15, "hydroxyl-containing" should read -- hydroxyl containing --;

Column 2, Formula I, and

Column 3, Formula II, "$R_x'$" should read -- $R'_x$ --;

Column 3, line 61, before "esters" insert -- as --;

Column 4, line 14, "derivitives" should read -- derivatives --;

Column 4, line 54, after "be" insert -- a --;

Column 5, line 5, "t-tubylamine" should read -- t-butylamine --;

Column 5, line 21, "2,2-dimethyl-1,3-bis[3(N-morpholinylpropionyl]-pro-" should read -- 2,2-dimethyl-1,3-bis[3(N-morpholinylpropionyloxy]-pro- --;

UNITED STATES PATENT AND TRADEMARK OFFICE
CERTIFICATE OF CORRECTION

PATENT NO. : 4,199,420

DATED : April 22, 1980

INVENTOR(S) : James M. Photis

It is certified that error appears in the above-identified patent and that said Letters Patent are hereby corrected as shown below:

Column 6, line 2, after "if" insert -- desired, be --;

Column 6, line 56, "occured" should read -- occurred --;

Column 6, line 56, "6" should read -- 8 --;

Column 7, line 47, "ACTOMER X.80® 1" should read -- ACTOMER X-80® 1 -- same in footnote 1;

Column 8, line 21, "ACTOMER X.80® 1" should read -- ACTOMER X-80® 1 -- same in footnote 1;

Column 8, line 58, "ACTOMER X.80® 1" should read -- ACTOMER X-80® 1 -- same in footnote 1;

Column 8, line 62, footnote 1, "alkyl" should read -- alkyd --;

In the Claims

Claim 1, column 9, line 5, "alkoxysubstituted" should read -- alkoxy substituted --;

UNITED STATES PATENT AND TRADEMARK OFFICE
CERTIFICATE OF CORRECTION

PATENT NO. : 4,199,420　　　　　　　　　　　　Page 3 of 3
DATED　　　 : April 22, 1980
INVENTOR(S) : James M. Photis It is certified that error appears in the above-identified patent and that said Letters Patent are hereby corrected as shown below:

Claim 7, line 33, "ysubstituted" should read -- y substituted --;

Claim 11, after "wherein" delete "in", and

Claim 14, after "wherein" delete "in".

Signed and Sealed this

*Ninth* Day of *September 1980*

[SEAL]

*Attest:*

SIDNEY A. DIAMOND
*Attesting Officer*　　　*Commissioner of Patents and Trademarks*